United States Patent
Chen et al.

(10) Patent No.: US 11,554,356 B2
(45) Date of Patent: Jan. 17, 2023

(54) FULL CONTINUOUS FLOW PREPARATION METHOD OF 2-METHYL-4-AMINO-5-AMINOMETHYLPYRIMIDINE

(71) Applicant: Fudan University, Shanghai (CN)

(72) Inventors: Fener Chen, Shanghai (CN); Meifen Jiang, Shanghai (CN); Minjie Liu, Shanghai (CN); Huashan Huang, Shanghai (CN); Dang Cheng, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 17/467,091

(22) Filed: Sep. 3, 2021

(65) Prior Publication Data

US 2021/0394150 A1  Dec. 23, 2021

(30) Foreign Application Priority Data

Apr. 1, 2021 (CN) .......................... 202110358486.6

(51) Int. Cl.
*B01J 19/00* (2006.01)
*B01J 25/02* (2006.01)
*C07D 239/42* (2006.01)

(52) U.S. Cl.
CPC ........... *B01J 19/0093* (2013.01); *B01J 25/02* (2013.01); *C07D 239/42* (2013.01);
(Continued)

(58) Field of Classification Search
CPC ......... B01J 8/00; B01J 8/02; B01J 8/06; B01J 8/065; B01J 19/00; B01J 19/0093;
(Continued)

(56) References Cited

U.S. PATENT DOCUMENTS 2,820,050 A   1/1958  Hultquist
3,689,498 A   9/1972  Leimgruber et al.
(Continued)

FOREIGN PATENT DOCUMENTS

CN   103261173 A   8/2013
DE   2323845 A1    11/1973
(Continued)

OTHER PUBLICATIONS

Todd artd Bergel.a method for preparing 2-methyl-4-amino-5-aminomethyl pyrimidine through hydrolysis of 2-methyl-4-amino-5-acetamidomethyl pyrimidine.(J. Chem. Soc., 1937, 364).
(Continued)

*Primary Examiner* — Natasha E Young

(57) ABSTRACT

A full continuous flow preparation method of 2-methyl-4-amino-5-aminomethylpyrimidine. A mixed solution of cyanoacetamide, N,N-dimethylformamide and a catalyst is mixed with phosphorus oxychloride in a first micro-mixer, and then the reaction mixture undergoes continuous flow reaction in a microchannel reactor to obtain (dimethylaminomethylene) malononitrile. The reaction mixture is subjected to continuous quenching, extraction and separation, and the organic phase is concentrated, mixed with a methanol solution, and then reacted with an organic base to obtain 2-methyl-4-amino-5-cyanopyrimidine. After the mixed liquid is continuously filtered, the filter cake is dissolved in methanol, mixed with hydrogen in a second micro-mixer, and then transported to a fixed-bed reactor for hydrogenation reaction. The products are concentrated, dried and purified to obtain the desired 2-methyl-4-amino-5-aminomethylpyrimidine.

15 Claims, 2 Drawing Sheets

(52) U.S. Cl.
CPC ............... *B01J 2219/00804* (2013.01); *B01J 2219/00889* (2013.01); *B01J 2219/00909* (2013.01); *B01J 2219/00961* (2013.01); *B01J 2219/00963* (2013.01)

(58) Field of Classification Search
CPC ... B01J 23/00; B01J 23/70; B01J 23/74; B01J 23/755; B01J 25/00; B01J 25/02; B01J 2219/00; B01J 2219/00781; B01J 2219/00889; B01J 2219/00905; B01J 2219/00909; B01J 2219/0095; B01J 2219/00952; B01J 2219/00954; B01J 2219/00959; B01J 2219/00961; B01J 2219/00963; B01J 2219/00984; C07D 239/00; C07D 239/02; C07D 239/24; C07D 239/28; C07D 239/32; C07D 239/42

See application file for complete search history.

(56) References Cited

U.S. PATENT DOCUMENTS

| | | |
|---|---|---|
| 3,792,076 A | 2/1974 | Leimgruber et al. |
| 3,853,946 A | 12/1974 | Leimgruber et al. |
| 3,901,888 A | 8/1975 | Leimgruber et al. |
| 6,932,951 B1 * | 8/2005 | Losey ................. B01J 19/0093 422/213 |

FOREIGN PATENT DOCUMENTS

| | | | |
|---|---|---|---|
| GB | 772256 A | 4/1957 | |
| GB | 2118172 A * | 10/1983 | ........... C07D 239/42 |
| WO | 2012075677 A1 | 6/2012 | |

OTHER PUBLICATIONS

Fener Chen et al. 2-methyl-4-amino-5-cyanopyrimidine was catalytically hydrogenated to prepare 2-methyl-4-amino-5-aminomethyl pyrimidine.(Org. Process. Res. Dev., 2012, 16, 57).

* cited by examiner

FULL CONTINUOUS FLOW PREPARATION METHOD OF 2-METHYL-4-AMINO-5-AMINOMETHYLPYRIMIDINE

CROSS-REFERENCE TO RELATED APPLICATIONS

This application claims the benefit of priority from Chinese Patent Application No. 202110358486.6, filed on Apr. 1, 2021. The content of the aforementioned application, including any intervening amendments thereto, is incorporated herein by reference in its entirety.

TECHNICAL FIELD

The present disclosure relates to chemical synthesis, and specifically to a full continuous flow preparation method of 2-methyl-4-amino-5-aminomethylpyrimidine.

BACKGROUND

2-Methyl-4-amino-5-aminomethylpyrimidine (4) is an important intermediate for the synthesis of vitamin Bi. Vitamin Bi, as an important basic nutrient component, plays a significant role in protecting the nervous system, strengthening gastrointestinal motility, promoting carbohydrate digestion, improving the mental status and maintaining the normal activities of the nervous system, muscles, and heart. Moreover, it is also effective for the treatment of shingles. The synthesis and preparation of vitamin Bi has always attracted much attention.

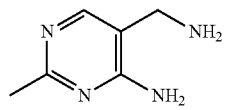

4

U.S. Pat. Nos. 3,689,498, 3,792,076, 3,853,946, 3,901,888 and 2,820,050, UK Patent No. 772256, German Patent No. 2323845, and Todd and Bergel et al. (*J. Chem. Soc.*, 1937, 364) all describe a method for preparing 2-methyl-4-amino-5-aminomethylpyrimidine by hydrolysis of 4-amino-5-acetaminomethylpyrimidine. In this method, the synthetic route of 2-methyl-4-amino-5-acetamidomethylpyrimidine is long, the process is complicated and costly, which is less environmental friendly, and is thus difficult for industrial application. World Patent No. WO2012/075677, Chinese Patent No. 103261173 and Chen Fener et al. (*Org. Process. Res. Dev.*, 2012, 16, 57) all describe the preparation of compound (I) from 2-methyl-4-amino-5-cyanopyrimidine through catalytic hydrogenation. This method uses cheap cyanoacetamide as the starting material, first dehydrates the cyanoacetamide in situ to produce malononitrile, then reacts with Vilsmeier reagent to prepare (dimethylaminomethylene) malononitrile, and then condenses with hydrochloric acid acetamidine to produce 2-methyl-4-amino-5-cyanopyrimidine. Though this method has readily-available raw materials, low cost and shortened synthesis process of 2-methyl-4-amino-5-cyanopyrimidine, it still struggles with the following outstanding shortcomings, such as time-consuming reaction process, poor conversion rate, harsh reaction conditions (the hydrogenation reaction is required to be performed under high pressure), large safety risk, high energy consumption and low yield. The above methods are all carried out in a traditional batch reactor. Therefore, considering the limitations of the existing preparation methods, there is an urgent need for those skilled in the art to develop a continuous preparation method with less time consumption, lower energy consumption and higher process efficiency and safety.

SUMMARY

In order to overcome the shortcomings of long reaction time, high safety hazard, high energy consumption and low efficiency in the traditional synthesis method using a batch reactor, the present disclosure provides a full continuous flow preparation method of 2-methyl-4-amino-5-aminomethylpyrimidine. This method greatly shortens the reaction time, significantly improves the product yield, automation degree and process efficiency and reduces energy consumption, so that the safety is greatly enhanced, and thus it is suitable for industrial application.

The present disclosure provides a full continuous flow preparation method of 2-methyl-4-amino-5-aminomethylpyrimidine. Use a micro-reaction system consisting of a micro-mixer, a microchannel reactor, continuous distillation and concentration, a continuous oscillating reactor, continuous filtration and continuous quenching, extraction and separation equipment that are connected in sequence, and the method comprises:

(1) transporting a mixture of cyanoacetamide, N,N-dimethylformamide and a catalyst, and phosphorus oxychloride separately into the first micro-mixer for uniform mixing; allowing the reaction mixture in the first micro-mixer to flow into the microchannel reactor followed by continuous flow reaction;

(2) feeding the reaction mixture flowing out of the microchannel reactor, an aqueous solution of an inorganic base and a first organic solvent into the continuous quenching-extraction-separation unit simultaneously for continuous quenching, extraction and separation to collect an organic phase;

(3) subjecting the organic phase to continuous concentration to obtain an oily product; dissolving the oily product with a second organic solvent followed by feeding to the second micro-mixer together with an acetamidine hydrochloride solution for uniform mixing; transporting the reaction mixture in the second micro-mixer to the continuous oscillating reactor for condensation and cyclization; feeding the reaction mixture flowing out of the continuous oscillating reactor to the continuous filtration unit for continuous filtration to collect a filter cake; and dissolving the filter cake in a first alkali-containing organic solution to produce a (dimethylaminomethylene) malononitrile organic solution followed by transportation to a first liquid storage buffer tank for collection;

(4) transporting the (dimethylaminomethylene) malononitrile organic solution in the first liquid storage buffer tank and hydrogen gas to the third micro-mixer for mixing, and then allowing the reaction mixture in the third micro-mixer to enter the fixed-bed reactor for continuous catalytic hydrogenation, wherein the fixed-bed reactor is filled with a Raney nickel catalyst; and (5) collecting the reaction mixture flowing out of the fixed-bed reactor followed by vacuum concentration, separation and purification to obtain a target product 2-methyl-4-amino-5-aminomethylpyrimidine;

as shown in the following reaction scheme:

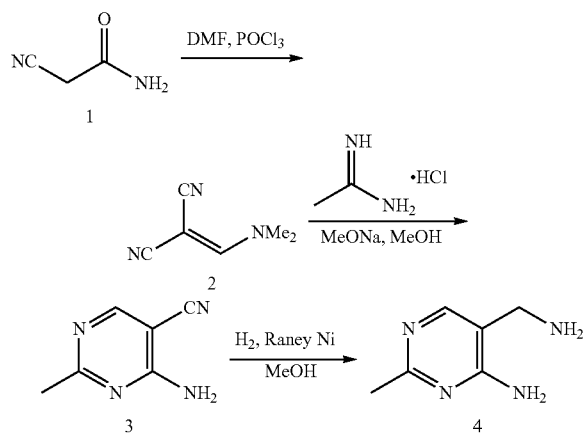

wherein compound (1) is cyanoacetamide; compound (2) is an intermediate [(dimethylamino)methylene] malononitrile; compound (3) is an intermediate 2-methyl-4-amino-5-cyanopyrimidine; and compound (4) is 2-methyl-4-amino-5-aminomethylpyrimidine.

In an embodiment, the catalyst in step (1) is a pyridine compound; and a molar ratio of cyanoacetamide, N,N-dimethylformamide, the catalyst and phosphorus oxychloride in step (1) is 1:(1-10):(0.05-0.8):(1-10). More preferably, the catalyst is pyridine; the molar ratio of cyanoacetamide, N,N-dimethylformamide, the catalyst and phosphorus oxychloride in step (1) is 1:(2-6):(0.05-0.3):(2-8).

In an embodiment, the microchannel reactor consists of a first part and a second part; a reaction temperature of the first part is −20-80° C., and a reaction temperature of the second part is −20-80° C.; a residence time of the reaction mixture in the first part is 0.2-30 minutes, and a residence time of the reaction mixture in the second part is 1-60 minutes; and a back pressure of the microchannel reactor is 0.1-5 MPa. In an embodiment, the reaction temperature of the first part of the microchannel reactor is −20-20° C., and the reaction temperature of the second part is 20-80° C.; the residence time of the mixed reaction materials in the two parts is 0.5-15 minutes and 5-35 minutes, respectively; and the back pressure of the microchannel reactor is 0.3-3 MPa.

In an embodiment, the mass fraction of the inorganic base in the aqueous solution of the inorganic base in step (2) is 5-50%; the inorganic base is selected from the group consisting of lithium carbonate, sodium carbonate, potassium carbonate, lithium bicarbonate, sodium bicarbonate, potassium bicarbonate, lithium hydroxide, sodium hydroxide, and potassium hydroxide and a combination thereof; a pH value of the crude product mixture after quenching is 2-10.

In an embodiment, the mass fraction of the inorganic base in the aqueous solution of the inorganic base in step (2) is 10-40%; the inorganic base is selected from the group consisting of sodium carbonate, potassium carbonate, sodium bicarbonate, potassium bicarbonate, sodium hydroxide, and potassium hydroxide and a combination thereof; a pH value of the crude product mixture after quenching is 3-9.

In an embodiment, the first organic solvent is a halogenated hydrocarbon solvent, an acetate solvent, a substituted benzene solvent or an alkyl ether solvent; the extraction is performed at a temperature of 0-50° C.; and a residence time of the reaction mixture in each extraction separator of the continuous quenching-extraction-separation unit is 0.1-30 minutes. More preferably, the first organic solvent is a halogenated hydrocarbon solvent, an acetate solvent; the extraction temperature is 15-35° C.; the extraction time is 0.1-20 minutes.

In an embodiment, in step (3), the acetamidine hydrochloride solution is prepared by dissolving acetamidine hydrochloride with a second alkali-containing organic solution at −20-35° C. and filtration; a molar concentration of acetamidine hydrochloride in the acetamidine hydrochloride solution is 0.5-7 mol/L; an alkali in the second alkali-containing organic solution is selected from the group consisting of sodium hydroxide, potassium hydroxide, sodium methoxide, potassium methoxide, sodium ethoxide, potassium ethoxide, potassium tert-butoxide and sodium tert-butoxide; an organic solvent used in the second alkali-containing organic solution is one or more of $C_1$-$C_6$ fatty alcohols; a molar ratio of the acetamidine hydrochloride to the alkali in the acetamidine hydrochloride solution is 1:0.7-3. In an embodiment, an alkali in the second alkali-containing organic solution is selected from the group consisting of sodium methoxide, potassium methoxide, sodium ethoxide, potassium ethoxide, potassium tert-butoxide and sodium tert-butoxide; an organic solvent used in the second alkali-containing organic solution is methanol, ethanol, isopropanol, 1,2-propanediol, 1,3-propanediol and 1-butanol; and the molar ratio of acetamidine hydrochloride to alkali is controlled within the range of 1:0.8-2.

In an embodiment, a molar ratio of (dimethylaminomethylene) malononitrile to acetamidine hydrochloride in the (dimethylaminomethylene) malononitrile organic solution is 1:0.6-5. More preferably, the molar ratio of (dimethylaminomethylene) malononitrile to acetamidine hydrochloride is 1:0.8-3.

In an embodiment, the organic solvent used in step (3) is one or more of $C_1$-$C_6$ fatty alcohols, preferably methanol, ethanol, isopropanol, 1,2-propanediol, 1,3-propanediol or 1-butanol.

In an embodiment, the continuous oscillating reactor in step (3) is a continuous flow reactor for three-phase mixing of solid, liquid and gas; and a temperature in the continuous oscillating reactor is −10-65° C.; a residence time of the reaction mixture in the continuous oscillating reactor is 10-120 minutes; the continuous filtration is performed at a temperature of −10-45° C. In an embodiment, the temperature in the reactor is −5-55° C.; the residence time of the reaction mixture in the reactor is 15-110 minutes; and the continuous filtration is performed at 0-35° C.

In an embodiment, the fixed-bed reactor in step (4) is filled with modified Raney nickel catalyst, or a mixture of modified Raney nickel catalyst and quartz sand, or a mixture of a modified Raney nickel catalyst and a molecular sieve, or an unmodified Raney nickel catalyst, or a mixture of an unmodified Raney nickel catalyst and quartz sand. More preferably, the fixed-bed reactor is filled with the modified Raney nickel catalyst, or a mixture of the modified Raney nickel catalyst and quartz sand.

In an embodiment, in step (4), an alkali in the (dimethylaminomethylene) malononitrile organic solution is an inorganic base or an organic base; the inorganic base is ammonia or hydrazine hydrate; and the organic base is selected from the group consisting of methylamine, urea, ethylamine, ethanolamine, ethylenediamine, dimethylamine, trimethylamine, triethylamine, propylamine, isopropylamine, 1,3-propanediamine, 1,2-propanediamine, tripropylamine, triethanolamine, butylamine, isobutylamine, tert-butylamine, tributylamine, hexylamine, octylamine, aniline, benzylamine, cyclohexylamine and pyridine; and a molar ratio of 2-methyl-4-amino-5-cyanopyrimidine to the alkali agent is 1:(0.1-10). More preferably, the alkali agent is an inorganic base or an organic base; the inorganic base is ammonia; and the organic base is selected from the group consisting of methylamine, ethylamine, ethylenediamine, dimethylamine, trimethylamine, triethylamine, propylamine and pyridine; the molar ratio of 2-methyl-4-amino-5-cyanopyrimidine to the alkali agent is 1:(0.1-5).

In an embodiment, in step (4), the temperature in the third micro-mixer is controlled at 5-150° C.; the temperature in the fixed-bed reactor is controlled at 20-150° C.; flow rates of the reaction mixture entering the third micro-mixer and the hydrogen are adjusted such that a molar ratio of 2-methyl-4-amino-5-cyanopyrimidine to hydrogen is 1:(0.95-1.4); a residence time of the reaction mixture in the fixed-bed reactor is 0.01-60 minutes; and a back pressure valve of the fixed-bed reactor is 0.1-6 MPa. More preferably, the temperature in the third micro-mixer is controlled at 25-110° C.; the temperature in the fixed-bed reactor is controlled at 25-130° C.; the molar ratio of 2-methyl-4-amino-5-cyanopyrimidine to hydrogen is 1:(1-1.3); the residence time of the reaction mixture in the fixed-bed reactor is 0.1-45 minutes; and a back pressure of the back pressure valve is set to 0.1-4 MPa.

In an embodiment, the first micro-mixer, the second micro-mixer and the third micro-mixer are independently a static mixer, a T-type micro-mixer, a Y-type micro-mixer, a cross-type mixer, a coaxial flow micro-mixer or a flow-focusing micro-mixer, preferably any one of cross-type mixer, coaxial flow micro-mixer and flow-focusing micro-mixer. The first micro-mixer and the third micro-mixer are both controlled at a temperature of −10-50° C., preferably 0-30° C.

In an embodiment, the microchannel reactor in step (1) is a tubular microchannel reactor, a plate microchannel reactor or other types of microchannel reactors already on the market.

In an embodiment, the inner diameter of the tubular microchannel reactor is 50 μm-10 mm, preferably 100 μm-5 mm. The plate microchannel reactor includes a first heat exchange layer, a reaction layer, and a second heat exchange layer sequentially arranged from top to bottom; the reaction layer is provided with a reaction fluid channel, and a hydraulic diameter of the reaction fluid channel is 50 μm-10 mm, preferably 100 μm-5 mm.

In an embodiment, the continuous extraction separator in step (2) is a plate microchannel extraction separator, a membrane extraction separator, an annulus centrifugal extraction separator or other types of continuous extraction and separation equipment already on the market. The inner diameter of the plate type continuous extraction separator is 100 μm-10 mm, including a mixed layer and a separation layer; the membrane of the membrane extraction separator is a hydrophobic membrane with a pore size of 0.1-4 μm; the diameter of the annulus centrifugal extraction and separation device is 10 cm-1 m, and one or more plate-type continuous extraction separators or membrane-type extraction separators are connected in series to form the quenching-extraction-separation unit.

In an embodiment, the continuous oscillating reactor in step (3) is a serial continuous oscillating stirred tank reactor, or a tubular continuous oscillating and re-entrant flow reactor, or a continuous flow reactor that can achieve full solid-liquid mixing already on the market.

In an embodiment, the fixed-bed reactor in step (4) is a jacketed fixed-bed reactor or a non-jacketed oil bath fixed-bed reactor.

In an embodiment, the inner diameter of the fixed-bed reactor is 100 μm-50 cm, and a length of 2 cm-50 cm, one or more units can be connected in series to form an operating unit.

In an embodiment, the micro-reaction system in step (1) includes a feed pump, a micro-mixer, a microchannel reactor and a back pressure valve. One inlet of the micro-mixer is configured to the feed pump of the mixed solution of cyanoacetamide, N,N-dimethylformamide and the catalyst, the other inlet of the micro-mixer is connected to the feed pump of phosphorus oxychloride, and the outlet of the micro-mixer is connected with the inlet of the microchannel reactor, and the outlet of the microchannel reactor is connected with the back pressure valve; the outlet of the back pressure valve is connected to one inlet of the continuous quenching, extraction and separation equipment in step (2), and the remaining two inlets are respectively connected to a feed pump of the aqueous solution of inorganic alkali and a feed pump of the organic solvent, the water phase outlet of the separation equipment is connected to a water phase receiving device, and the organic phase outlet is connected to the inlet of the concentration device in step (3); and the other controllable valve inlet of the continuous rotary evaporation device is connected with another organic solvent feed pump.

In an embodiment, the continuous reaction system in step (3) comprises a feed pump, a micro-mixer, a continuous oscillating reactor and a continuous filtration device; one inlet of the micro-mixer is connected with the reaction liquid feed pump, and the other inlet of the micro-mixer is connected with the outlet of the continuous concentration device; an outlet of the micro-mixer is connected with the inlet of the continuous oscillating reactor, the outlet of the continuous oscillating reactor is connected to the first port of the continuous filter, and the second port of the continuous filter is connected to the feed pump of the organic solvent for dissolving the filter cake produced by the continuous filter; the first outlet of the continuous filter is connected to the filtrate collecting device, the second outlet is connected to the inlet of the liquid storage buffer tank, and the outlet of the liquid storage buffer tank is connected to a feed pump of the next microchannel reaction system.

As a preferred technical solution, the micro-reaction system in step (4) comprises a feed pump, a gas mass flow controller, a fixed-bed reactor, a gas-liquid separator, and a liquid storage buffer tank and a back pressure valve. One inlet of the fixed-bed reactor is connected to the reaction liquid feed pump, and the other inlet of the microchannel reactor is connected to a gas mass flow controller; the outlet of the fixed-bed reactor is connected to the first port on the top of the gas-liquid separator, and the second port on the top of the gas-liquid separator is connected to nitrogen to provide pressure to the gas-liquid separator, the pressure of the nitrogen is adjustable in range of 0.01-3.5 MPa; the back pressure valve is connected to the third interface on the top of the gas-liquid separator, and the back pressure range of the back pressure valve is 0.01-3 MPa, the pressure value of the nitrogen gas is 0.02-0.5 MPa greater than the back pressure value set by the back pressure valve; and the liquid outlet of the gas-liquid separator is connected to the inlet of the liquid storage buffer tank.

In an embodiment, the step (5) is performed through steps of:

subjecting the reaction mixture in the liquid storage buffer tank collected from the fixed-bed reactor to vacuum concentration, separation and purification to obtain an off-white solid product 2-methyl-4-amino-5-aminomethylpyrimidine (4).

The continuous preparation of 2-methyl-4-aminomethylpyrimidine (4) provided herein can be applied to the industrial production of 2-methyl-4-amino-5-aminomethylpyrimidine through the strategy of multi-channel parallel amplification.

Compared to the traditional preparation of 2-methyl-4-amino-5-aminomethylpyrimidine (4) using a batch reactor, this application has the following beneficial effects.

1. The full continuous flow microchannel reaction system has excellent mass transfer, heat transfer and molecular mixing properties, which greatly shortens the reaction time from several days (in a traditional batch reactor) to a few hours and improves the reaction efficiency. Moreover, the reaction process can be quantitatively monitored, and the side reactions can be significantly suppressed. Compared to the traditional synthesis method, the yield of the product 2-methyl-4-amino-5-aminomethylpyrimidine (4) is increased from about 60% to 90%, and the purity is improved from about 95% to 98%.

2. The method provided herein has full continuous synthesis process, high automation degree, good space-time efficiency, less labor intensity and low cost.

3. In the preparation method provided herein, the multi-phase mixing, mass transfer and reaction are all completed in the micro-mixer and the microchannel reactor, which leads to mild conditions and simple operation. Moreover, the stirring device is not needed, which facilitates reducing the energy consumption. As a consequence, the method is suitable for the industrial production.

4. The full continuous flow method has simple quenching-extraction-separation operations, fast quenching speed, high safety, good separation effect (the separation yield is close to the reaction yield) and desirable extraction efficiency. The reaction process and the liquid-liquid extraction and separation process are continuously carried out, which greatly improves the overall process efficiency and the purity of the target product.

Figure 1:
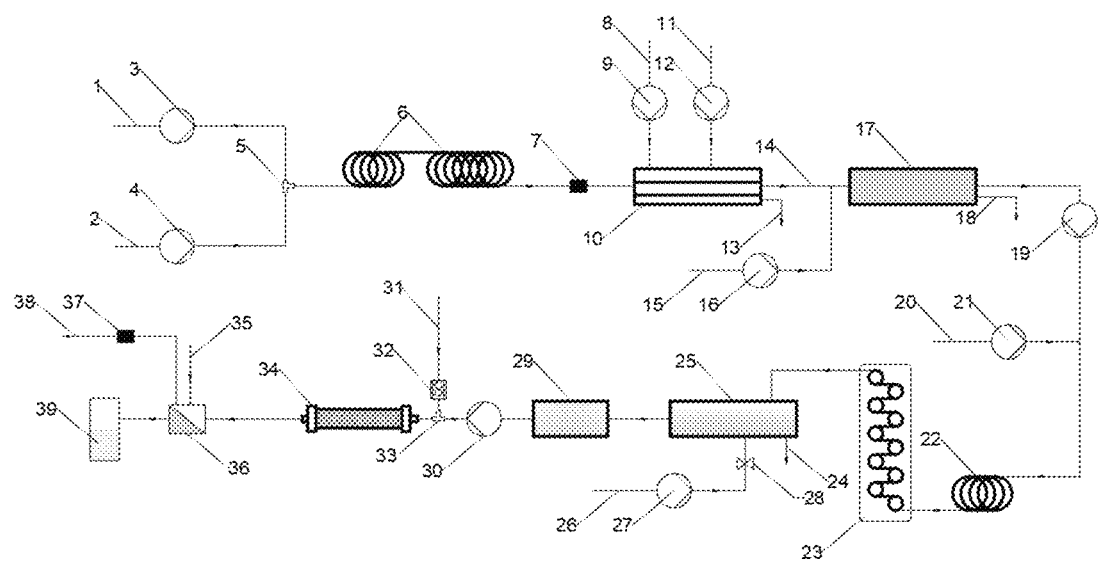
FIG. 1 is a schematic diagram of a structure of a micro-reaction system according to an embodiment of the present disclosure.

In the drawings: 1: phosphorus oxychloride pipeline; 2: cyanoacetamide pipeline: 3: first feed pump; 4: second feed pump; 5: first micro-mixer; 6: microchannel reactor; 7: first back pressure valve, 8: inorganic alkali solution pipeline; 9: third feed pump; 9a: first liquid storage buffer tank; 9b: fourth feed pump; 10: continuous extraction separator; 11: first organic solvent pipeline; 12: fifth feed pump; 13: aqueous phase outlet pipeline; 14: organic phase outlet pipeline; 14a: second liquid storage buffer tank; 15: second organic solvent pipeline; 16: sixth feed pump; 17: continuous vacuum concentration unit; 18: waste liquid collection bottle; 19: seventh feed pump; 19a: alkali-containing organic solution-acetamidine hydrochloride mixture pipeline; 19b: eighth feed pump; 19c: first valve; 19d: continuous filter; 19e: acetamidine hydrochloride solution; 20: third liquid storage buffer tank; 21: ninth feed pump; 22: second micro-mixer; 23: continuous oscillating reactor; 24: filtrate pipeline; 25: continuous filter; 26: third organic solvent pipeline; 27: tenth feed pump; 28: second valve; 29: fourth liquid storage buffer tank; 30: eleventh feed pump; 31: hydrogen pipeline; 32: hydrogen gas mass flow controller; 33: third micro-mixer; 34: fixed-bed reactor; 35: nitrogen pipeline; 36: gas-liquid separator; 37: second back pressure valve; 38: exhaust gas output pipeline; 39: product storage buffer tank; 10-1: organic solvent inlet; 10-2: reaction mixture inlet; 10-3: inorganic alkali solution inlet; 10-4: organic phase outlet; and 10-5: aqueous phase outlet.

DETAILED DESCRIPTION OF EMBODIMENTS

In order to make the technical solutions, structural features, objectives and beneficial effects of the disclosure clearer, the disclosure will be described in detail below with reference to the embodiments and accompanying drawings. It should be noted that these embodiments are merely illustrative, and are not intended to limit the disclosure.

Referring to an embodiment shown in FIG. 1, the micro-reaction system includes a phosphorus oxychloride pipeline 1, a cyanoacetamide reaction liquid pipeline 2, a first feed pump 3, a second feed pump 4, a first micro-mixer 5, a microchannel reactor 6, a first back pressure valve 7, an inorganic alkali solution pipeline 8, a third feed pump 9, a continuous extraction separator 10, a first organic solvent pipeline 11, a fifth feed pump 12, an aqueous phase outlet pipeline 13, an organic phase outlet pipeline 14, a second organic solvent pipeline 15, a sixth feed pump 16, a continuous vacuum concentration unit 17, a waste liquid collection bottle 18, a seventh feed pump 19, a third liquid storage buffer tank 20, a ninth feed pump 21, a second micro-mixer 22, a continuous oscillating reactor 23, a filtrate pipeline 24, a continuous filter 25, a third organic solvent pipeline 26, a tenth feed pump 27, a second valve 28, a fourth liquid storage buffer tank 29, an eleventh feed pump 30, a hydrogen pipeline 31, a hydrogen gas mass flow controller 32, a third micro-mixer 33, a fixed-bed reactor 34, a nitrogen pipeline 35, a gas-liquid separator 36, a second back pressure valve 37, an exhaust gas output pipeline 38 and a product storage buffer tank 39.

One inlet of the first micro-mixer 5 is connected to the first feed pump 3, and the other inlet of the first micro-mixer 5 is connected to the second feed pump 4. An outlet of the first micro-mixer 5 is connected to an inlet of the microchannel reactor 6, and an outlet of the microchannel reactor 6 is connected to the first back pressure valve 7. An outlet of the first back pressure valve 7 is connected to one inlet of the continuous extraction separator 10, and the remaining two inlets of the continuous extraction separator 10 are respectively connected to the third feed pump 9 and the fifth feed pump 12. The aqueous phase outlet pipeline 13 is connected to the water phase receiving device, and the organic phase outlet pipeline 14 is connected to one inlet of the continuous vacuum concentration unit 17. The other inlet of the continuous vacuum concentration unit 17 is connected to the sixth feed pump 16. One inlet of the second micro-mixer 22 is connected to the seventh feed pump 19, and the other inlet of the second micro-mixer 22 is connected to the ninth feed pump 21. An outlet of the second micro-mixer 22 is connected to an inlet of the continuous oscillating reactor 23. An outlet of the continuous oscillating reactor 23 is connected to a first port of the continuous filter 25, and a second port of the continuous filter 25 is connected to the tenth feed pump 27. A first outlet of the continuous filter 25 is connected to a filtrate collecting device, and a second outlet is connected to an inlet of the fourth liquid storage buffer tank 29. An outlet of the fourth liquid storage buffer tank 29 is connected to the eleventh feed pump 30. One inlet of the third micro-mixer 33 is connected to the hydrogen gas mass flow controller 32, and the other inlet of the third micro-mixer 33 is connected to the eleventh feed pump 30. An outlet of the third micro-mixer 33 is connected to an inlet of the fixed-bed reactor 34. An outlet of the fixed-bed reactor 34 is connected to a first port on the top of the gas-liquid separator 36, and a second port on the top of the gas-liquid separator 36 is connected to the nitrogen pipeline 35 to introduce nitrogen. The second back pressure valve 37 is connected to a third port on the top of the gas-liquid separator 36. A liquid outlet of the gas-liquid separator 36 is connected to an inlet of the product storage buffer tank 39.

Figure 2:
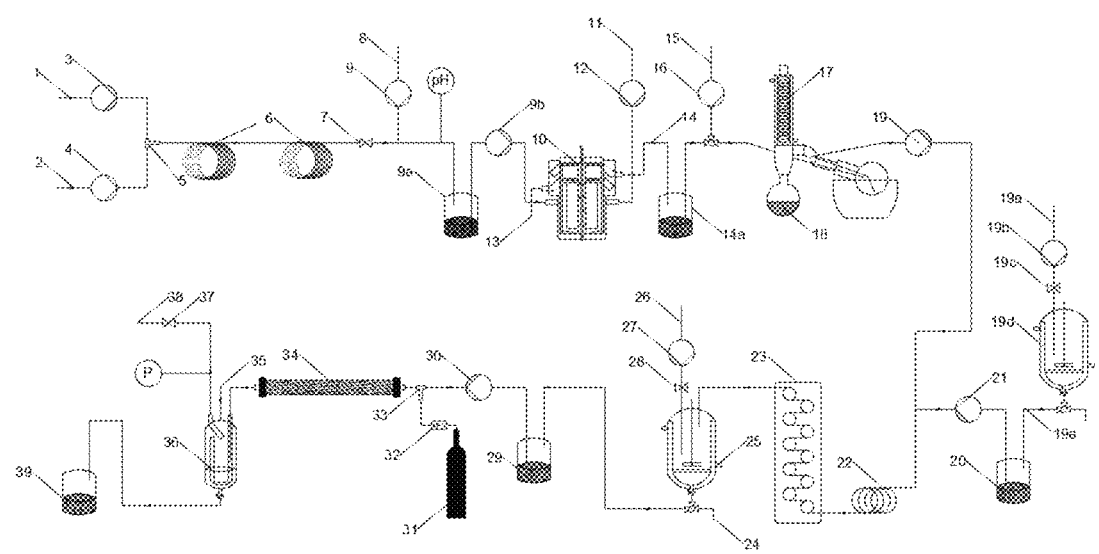
FIG. 2 is another schematic diagram of the structure of the micro-reaction system according to an embodiment of the present disclosure.
Figure 3:
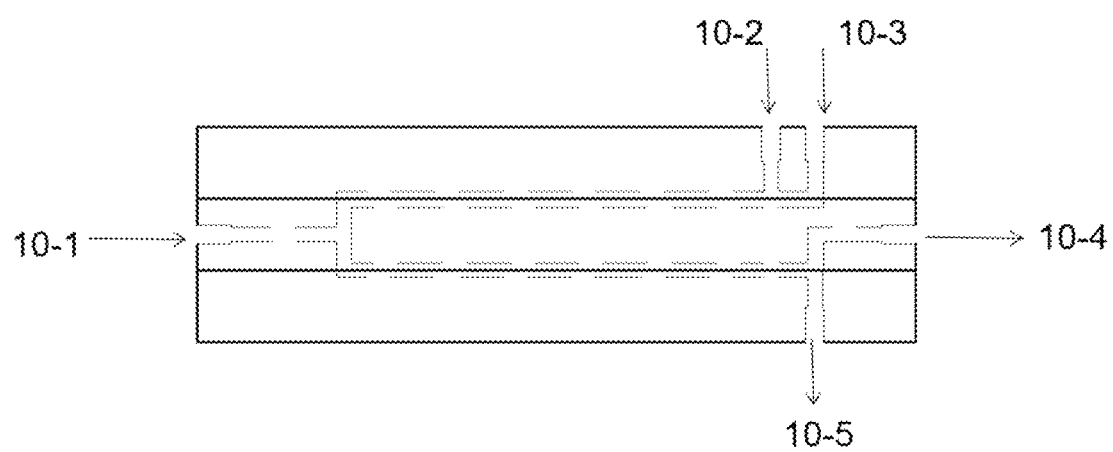
FIG. 3 is a schematic diagram of continuous quenching, extraction and separation equipment used in an embodiment of the present disclosure.

Referring to an embodiment illustrated in FIG. 2, the micro-reaction system of the disclosure includes a phosphorus oxychloride pipeline 1, a cyanoacetamide reaction liquid pipeline 2, a feed pump 3 and a second feed pump 4, a first micro-mixer 5, and a microchannel reactor 6, a first back pressure valve 7, an inorganic alkali solution pipeline 8, a third feed pump 9, a first liquid storage buffer tank 9a, a continuous extraction separator 10, a first organic solvent pipeline 11, a fifth feed pump 12, an aqueous phase outlet pipeline 13, an organic phase outlet pipeline 14, a second liquid storage buffer tank 14a, a second organic solvent pipeline 15, a sixth feed pump 16, a continuous vacuum concentration unit 17, a waste liquid collection bottle 18, a seventh feed pump 19, alkali-containing organic solution-acetamidine hydrochloride mixture pipeline 19a, a eighth feed pump 19b, a first valve 19c, a continuous filter 19d, an acetamidine hydrochloride solution 19e, a third liquid storage buffer tank 20, a ninth feed pump 21, a second micro-mixer 22, a continuous oscillation reactor 23, a filtrate pipeline 24, a continuous filter 25, a third organic solvent pipeline 26, a tenth feed pump 27, a second value 28, a fourth liquid storage buffer tank 29, a eleventh feed pump 30, a hydrogen pipeline 31, a hydrogen gas mass flow controller 32, a third micro-mixer 33, a fixed-bed reactor 34, a nitrogen pipeline 35, a gas-liquid separator 36, a second back pressure valve 37, a exhaust gas output pipeline 38, a product storage buffer tank 39.

One inlet of the first micro-mixer 5 is connected with the first feed pump 3, and the other inlet of the first micro-mixer 5 is connected with the second feed pump 4. An outlet of the first micro-mixer 5 is connected with an inlet of the microchannel reactor 6, and an outlet of the microchannel reactor 6 is connected to the first back pressure valve 7. The outlet of the first back pressure valve 7 is connected to the outlet of the third feed pump 9 and is connected to the first liquid storage buffer tank 9a. The outlet of the first liquid storage buffer tank 9a is connected to the fourth feed pump 9b, the outlet of the fourth feed pump 9b is connected to one of the inlets of the continuous extraction separator 10, the fifth feed pump 12, and the aqueous phase outlet pipeline 13 is connected to the water phase receiving device, the organic phase outlet 14 is connected to the second liquid storage buffer tank 14a, and the outlet of the second liquid storage buffer tank 14a is connected to an inlet of the continuous vacuum concentration unit 17. The other inlet of the continuous vacuum concentration unit 17 is connected to the sixth feed pump 16. The continuous filter 19d is connected to the eighth feed pump 19b through a first valve 19c. One inlet of the second micro-mixer 22 is connected to the seventh feed pump 19, and the other inlet of the second micro-mixer 22 is connected to the ninth feed pump 21. An outlet of the second micro-mixer 22 is connected to an inlet of the continuous oscillating reactor 23, and the outlet of the continuous oscillating reactor 23 is connected to the first port of the continuous filter 25. A second port of the continuous filter 25 is connected to the tenth feed pump 27. The first outlet of the continuous filter 25 is connected to the filtrate collecting device, and the second outlet is connected to the inlet of the fourth liquid storage buffer tank 29. An outlet of the fourth liquid storage buffer tank 29 is connected to the eleventh feed pump 30. One inlet of the third micro-mixer 33 is connected to the hydrogen gas mass flow controller 32, and the other inlet of the third micro-mixer 33 is connected to the eleventh feed pump 30. An outlet of the third micro-mixer 33 is connected to the inlet of the fixed-bed reactor 34. The outlet of the fixed-bed reactor 34 is connected to the first port on the top of the gas-liquid separator 36, the second port on the top of the gas-liquid separator 36 is connected to the nitrogen pipeline 35 to connect nitrogen, and the second back pressure valve 37 is connected to the third interface on the top of the gas-liquid separator 36. The liquid outlet of the gas-liquid separator 36 is connected to the inlet of the product storage buffer tank 39.

The working process of the micro-reaction system provided herein is described as follows.

(A) Phosphorus oxychloride and a mixed solution of cyanoacetamide, N,N-dimethylformamide and a catalyst are simultaneously pumped to the first micro-mixer 5 respectively through the first feed pump 3 and the second feed pump 4, and then undergo a continuous flow reaction in the microchannel reactor 6. Then, the reaction mixture flowing out of the microchannel reactor 6 enter into the continuous extraction separator 10, to which an aqueous solution of the inorganic base and an organic solvent are fed respectively through the third feed pump 9 and the fifth feed pump 12 to perform continuous quenching, extraction and separation. The organic phase flowing out of the continuous extraction separator 10 and the acetamidine hydrochloride solution are simultaneously pumped into the second micro-mixer 22 respectively through the seventh feed pump 19 and the ninth feed pump 21, and then the reaction mixture is transported to the continuous oscillating reactor 23 for the condensation and cyclization reaction. The outflowing reaction mixture enters the continuous filter 25 for continuous filtration, and the filter cake is dissolved with an alkali-containing organic solution which is pumped into the continuous filter 25 through the tenth feed pump 27, and the obtained reaction mixture is transported to the fourth storage buffer tank 29 for collection. The reaction mixture and hydrogen are simultaneously fed to third micro-mixer 33 for mixing respectively through the eleventh feed pump 30 and the hydrogen gas mass flow controller 32, and then the reaction mixture enters into the fixed-bed reactor 34 filled with a modified Raney nickel catalyst to undergo a continuous catalytic hydrogenation reaction. The reaction mixture flowing out of the fixed-bed reactor 34 then enter the gas-liquid separator 36, where the waste gas is discharged through the third port on the top of the gas-liquid separator 36 and the second back pressure valve 37, and the reaction liquid is discharged from the bottom outlet of the gas-liquid separator 36 to be collected into the product storage buffer tank 39, and then subjected to vacuum concentration to obtain the target product 2-methyl-4-amino-5-aminomethylpyrimidine.

In order to better illustrate the objectives, technical solutions and advantages of the present disclosure, the present disclosure will be further described below in conjunction with embodiments.

Example 1

A mixed solution of cyanoacetamide, N,N-dimethylformamide and pyridine, and phosphorus oxychloride were simultaneously transported to a first T-type micro-mixer and mixed at −10° C., and then the reaction mixture entered into the tube-type microchannel reactor with a total volume of 8 mL and a microchannel diameter of 0.8 mm, where the first part had a volume of 3 mL, and was kept at −10° C.; and the second part had a volume of 5 mL, and was maintained at 25° C. The concentration and flow rate of the raw materials were adjusted such that a molar ratio of cyanoacetamide to N,N-dimethylformamide to pyridine to phosphorus oxychloride was 1:3:0.1:3, and the back pressure of the back pressure valve was set at 0.7 MPa. After reacted for 15 min (that was, the residence time of the reaction mixture in the microchannel reactor was 15 min), the reaction mixture flowed out from the outlet of the back pressure valve.

The reaction mixture was immediately quenched with a saturated sodium bicarbonate solution, and detected to have a pH of 4. Meanwhile, the ethyl acetate was fed to the continuous extraction separator through another inlet for continuous extraction and separation. The organic phase was allowed to enter the continuous vacuum concentration unit and concentrated at 10 mbar and 50° C. The obtained oily product was dissolved in methanol, and then delivered to a second T-type micro-mixer together with the acetamidine hydrochloride solution through a feed pump, where a temperature of the second T-type micro-mixer was 25° C. The flow rate of the feed pump was adjusted such that a molar ratio of (dimethylaminomethylene) malononitrile (2) to acetamidine hydrochloride was 1:1.5. The reaction mixture was transported to a continuous oscillating reactor with a volume of 90 mL and underwent condensation and cyclization at 50° C. for 40 min. Then the reaction mixture flowing out of the continuous oscillating reactor directly entered the continuous filter and filtered at 30° C. to collect a filter cake, which was dissolved in a methanol solution containing 0.02 g/mL triethylamine and transported to the storage buffer tank for collection.

The modified Raney nickel catalyst (40-60 mesh) was filled in a tubular fixed-bed reactor (length: 20 cm; inner diameter: 1 cm). The reaction solution collected in the storage buffer tank and hydrogen were simultaneously transported to a third T-type micro-mixer and mixed at 90° C., where flow rates of the reaction solution and hydrogen were adjusted so that a molar ratio of 2-methyl-4-amino-5-cyanopyrimidine (3) to triethylamine to hydrogen was 1:0.1:1.3. The reaction mixture was then directly fed to the tubular fixed-bed reactor filled with the modified Raney nickel catalyst for reaction, where a reaction volume in the fixed-bed reactor filled with modified Raney nickel catalyst was about 2 mL; a back pressure of the back pressure valve was set to 1.6 MPa; a pressure of nitrogen introduced to the gas-liquid separator was adjusted to 1.9 MPa; and the reaction was performed at 110° C. for about 5 min. Then the reaction mixture flowed out from the outlet of the fixed-bed reactor and entered the gas-liquid separator for gas-liquid separation. The gas component was discharged, and the liquid was collected, concentrated and dried to obtain an off-white solid, where the substrate cyanoacetamide was completely converted, and the desired product 2-methyl-4-amino-5-aminomethylpyrimidine (4) had a yield of 90% and a purity greater than 98% (LC-MS).

Example 2

The preparation process provided in this example was basically the same as that in Example 1, except that in this example, the molar ratio of cyanoacetamide to N,N-dimethylformamide to the catalyst to phosphorus oxychloride was 1:2:0.05:2, and the reaction was performed at 80° C. for 18 min; the back pressure of the back pressure valve was set to 0.2 MPa; the reaction was quenched with a saturated sodium carbonate solution; and the first and second micro-mixers were Y-type micro-mixers. In this example, the substrate cyanoacetamide also experienced a complete conversion, and the target product 2-methyl-4-amino-5-aminomethylpyrimidine (4) had a yield of 89% and a purity of 93% (LC-MS).

Example 3

This example was the same as Example 1, the only difference was that after continuous quenching in this embodiment, the solution was entered into the storage buffer tank for collection, and then was transported to the annulus continuous extraction separator by the feed pump, the dichloride methane was used as the extraction solvent, and the extraction temperature was 25° C. The organic phase of the continuous extraction was entered into another storage buffer tank for collection, and then entered into the continuous vacuum concentration unit. The organic solvent ethanol was used to dissolve the oily product. The reaction temperature of the condensation and cyclization reaction was 35° C., and the reaction time was 60 minutes. After the product was filtered, the filter cake was dissolved with an ethanol solution containing ammonia water. The length of the fixed-bed reactor was 10 cm and the inner diameter was 1 cm. The product 2-methyl-4-amino-5-aminomethylpyrimidine (4) obtained in this example had a yield of 90.1% and a purity of 92.4% (LC-MS).

Example 4

This example was the same as Example 1, except that the molar ratio of cyanoacetamide, N,N-dimethylformamide, catalyst and phosphorus oxychloride in this example was 1:6:0.3:8. The reaction temperature was 0° C. in the first part and 25° C. in the second part. The reaction time was 30 minutes, and the back pressure value of the back pressure valve was set to 3 MPa. The quenched inorganic alkali solution was 25% sodium hydroxide solution, and after quenching, the pH value was determined to be 5. The organic solution of (dimethylaminomethylene) malononitrile was a mixed solution of methanol and ethanol, in which the molar ratio of (dimethylaminomethylene) malononitrile to acetamidine hydrochloride was 1:0.8. The microchannel fixed-bed reactor used in the hydrogenation reaction was filled with unmodified Raney nickel, and the molar ratio of 2-methyl-4-amino-5-cyanopyrimidine to the alkali agent dimethylamine used was 1:5. The molar ratio of 2-methyl-4-amino-5-cyanopyrimidine to hydrogen was 1:1. The product 2-methyl-4-amino-5-aminomethylpyrimidine (4) obtained in this example had a yield of 56% and a purity of 89% (LC-MS).

Example 5

This example was the same as Example 1, except that the molar ratio of cyanoacetamide, N,N-dimethylformamide, catalyst and phosphorus oxychloride in this example was 1:4:0.1:4. The reaction temperature was 50° C. The reaction time was 15 minutes, and the back pressure value of the back pressure valve was set to 1 MPa. After quenching the pH value was 7. The molar ratio of (dimethylaminomethylene) malononitrile to acetamidine hydrochloride was 1:5. The temperature of the hydrogenation reaction mixer was 100° C., and the temperature inside the reactor was 100° C. The molar ratio of 2-methyl-4-amino-5-cyanopyrimidine to the alkali ammonia water used was 1:1, and the molar ratio to hydrogen was 1:1. The reaction time was 5 minutes. The product 2-methyl-4-amino-5-aminomethylpyrimidine (4) obtained in this example had a yield of 75% and a purity of 90% (LC-MS).

Example 6

This example was the same as Example 1, except that the temperature of the continuous oscillating reactor in this example was controlled at 45° C. and the reaction time was 30 minutes. The temperature of continuous filtration was −5° C. The fixed-bed reactor used in the hydrogenation reaction was filled with modified Raney nickel and quartz sand with a weight ratio of 1:1. The product 2-methyl-4-amino-5-aminomethylpyrimidine (4) obtained in this example had a yield of 90.5% and a purity of 98% (LC-MS).

Example 7

This example was the same as Example 1, except that the continuous flow reactor used in step (1) in this example was a plate microchannel reactor. The volume of the first part of the reactor was 1.3 mL, the temperature was −20° C., and the volume of the second part was 8.3 mL, the temperature was 80° C., and the back pressure valve of the back pressure value was set to 2 MPa. The product 2-methyl-4-amino-5-aminomethylpyrimidine (4) obtained in this example had a yield of 88% and a purity of 97% (LC-MS).

Example 8

This example was the same as Example 1, except that the inorganic alkali solution for quenching in this example was a mixed solution of saturated sodium carbonate, saturated sodium bicarbonate and saturated potassium carbonate, and the pH value after quenching was 5.5. The product 2-methyl-4-amino-5-aminomethylpyrimidine (4) obtained in this example had a yield of 89% and a purity of 97% (LC-MS).

Example 9

This example was the same as Example 1, except that the organic solvent for continuous extraction used in this example was diethyl ether, and the product 2-methyl-4-amino-5-aminomethylpyrimidine (4) obtained in this example had a yield of 90%, and a purity of 96% (LC-MS).

Example 10

This example was the same as Example 1, except that the inorganic alkali aqueous solution for continuous quenching used in this example was a mixed solution of 20% sodium hydroxide solution and saturated potassium bicarbonate. The product 2-methyl-4-amino-5-aminomethylpyrimidine (4) obtained in this example had a yield of 91% and a purity of 98% (GC).

Example 11

This example was the same as Example 1, except that the continuous extraction separator in this example was a three-layer PTFE plate structure, and the microchannel between the first layer and the second layer had a filter membrane (filter hole 2.5 μm) to enhance the mixing effect, a hydrophobic membrane (a gap of 0.45 μm) was sandwiched in the microchannel between the second layer and the third layer to separate the aqueous phase and the organic phase. The extraction temperature was 25° C., and the resident time of the reaction mixture in the continuous extraction separator was 8 minutes. The product 2-methyl-4-amino-5-aminomethylpyrimidine (4) obtained in this example had a yield of 89% and a purity of 98% (LC-MS).

Example 12

This example was the same as Example 1, except that the fixed-bed reactor in this example was filled with a mixture of modified Raney nickel, molecular sieve and quartz sand, and the temperature of the reactor was controlled at 130° C. The resident time of the reaction mixture in the fixed-bed reactor was 20 minutes. The back pressure valve setting value was 4 MPa. In this example, the substrate cyanoacetamide was completely converted, and the resulting product 2-methyl-4-amino-5-aminomethylpyrimidine (4) had a yield of 89.7% and a purity of 94.2% (LC-MS).

Example 13

This example was the same as Example 1, except that the organic solvent used in the condensation and cyclization reaction in this example was isopropanol. In this example, the substrate cyanoacetamide was completely converted, and the resulting product 2-methyl-4-amino-5-aminomethylpyrimidine (4) had a yield of 90.8% and a purity of greater than 96% (LC-MS).

Example 14

This example was the same as Example 1, except that the solution was entered into the storage buffer tank for collection after continuous quenching, and the quenching temperature was 0° C. Then it was transported to an annulus continuous extraction separator by a feed pump, using dichloromethane as the extraction solvent, and the extraction temperature was 25° C. The organic phase of the continuous extraction was entered into another liquid storage buffer tank for collection, and then entered into the continuous vacuum concentration unit. The organic solvent used was n-butanol to dissolve the oily product. The reaction temperature of the condensation and cyclization reaction was 20° C., and the reaction time was 45 minutes. After the product was filtered, the filter cake was dissolved with an n-butanol solution containing triethanolamine. The fixed-bed reactor was a non-jacketed oil bath reactor, and the temperature of the oil bath was 125° C. The product 2-methyl-4-amino-5-aminomethylpyrimidine (4) obtained in this example had a yield of 87% and a purity of 92% (LC-MS).

Example 15

This example was the same as Example 1, except that the continuous oscillating reactor used in the condensation and cyclization reaction in this example was a tubular continuous oscillating reflux reactor. In this example, the substrate cyanoacetamide was completely converted, and the resulting product 2-methyl-4-amino-5-aminomethylpyrimidine (4) had a yield of 91.3% and a purity of more than 97% (LC-MS).

It should be noted that described above are merely preferred embodiments of the disclosure, which are not intended to limit the scope of the present disclosure. Any changes, replacements and modifications made by those skilled in the art without departing from the spirit of the disclosure should fall within the scope of the disclosure defined by the appended claims.

What is claimed is:

1. A method of preparing 2-methyl-4-amino-5-aminomethylpyrimidine in a full continuous-flow manner using a micro-reaction system, the micro-reaction system comprising a first micro-mixer, a microchannel reactor, a continuous quenching-extraction-separation unit, a continuous distillation-concentration unit, a second micro-mixer, a continuous oscillating reactor, a continuous filtration unit, a third micro-mixer and a fixed-bed reactor communicated in sequence, and the method comprising:
   (1) transporting a mixture of cyanoacetamide, N,N-dimethylformamide and a catalyst, and phosphorus oxychloride separately into the first micro-mixer for uniform mixing; allowing the reaction mixture in the first micro-mixer to flow into the microchannel reactor followed by continuous flow reaction;
   (2) feeding the reaction mixture flowing out of the microchannel reactor, an aqueous solution of an inorganic base and a first organic solvent into the continuous quenching-extraction-separation unit simultaneously for continuous quenching, extraction and separation to collect an organic phase;
   (3) subjecting the organic phase to continuous concentration to obtain an oily product; dissolving the oily product with a second organic solvent followed by feeding to the second micro-mixer together with an acetamidine hydrochloride solution for uniform mixing; transporting the reaction mixture in the second micro-mixer to the continuous oscillating reactor for condensation and cyclization; feeding the reaction mixture flowing out of the continuous oscillating reactor to the continuous filtration unit for continuous filtration to collect a filter cake; and dissolving the filter cake in a first alkali-containing organic solution to produce a (dimethylaminomethylene) malononitrile organic solution followed by transportation to a first liquid storage buffer tank for collection;
   (4) transporting the (dimethylaminomethylene) malononitrile organic solution in the first liquid storage buffer tank and hydrogen gas to the third micro-mixer for mixing, and then allowing the reaction mixture in the third micro-mixer to enter the fixed-bed reactor for continuous catalytic hydrogenation, wherein the fixed-bed reactor is filled with a Raney nickel catalyst; and
   (5) collecting the reaction mixture flowing out of the fixed-bed reactor followed by vacuum concentration, separation and purification to obtain a target product 2-methyl-4-amino-5-aminomethylpyrimidine;
   as shown in the following reaction scheme:

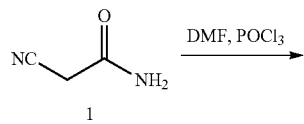

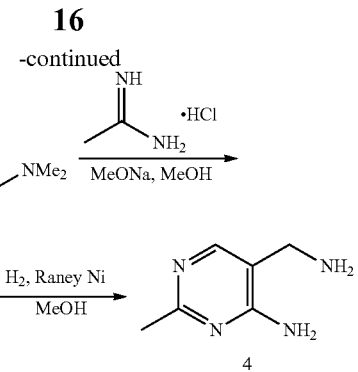

wherein compound (1) is cyanoacetamide; compound (2) is an intermediate [(dimethylamino)methylene] malononitrile; compound (3) is an intermediate 2-methyl-4-amino-5-cyanopyrimidine; and compound (4) is 2-methyl-4-amino-5-aminomethylpyrimidine.

2. The method of claim 1, wherein in step (1), the catalyst is a pyridine compound; and a molar ratio of cyanoacetamide to N,N-dimethylformamide to the catalyst to phosphorus oxychloride is 1: (1-10): (0.05-0.8): (1-10).

3. The method of claim 1, wherein in step (1), the microchannel reactor consists of a first part and a second part; a reaction temperature of the first part is −20-80° C., and a reaction temperature of the second part is −20-80° C.; a residence time of the reaction mixture in the first part is 0.2-30 minutes, and a residence time of the reaction mixture in the second part is 1-60 minutes; and a back pressure of the microchannel reactor is 0.1-5 MPa.

4. The method of claim 1, wherein in step (2), a mass fraction of the inorganic base in the aqueous solution of the inorganic base is 5-50%; the inorganic base is selected from the group consisting of lithium carbonate, sodium carbonate, potassium carbonate, lithium bicarbonate, sodium bicarbonate, potassium bicarbonate, lithium hydroxide, sodium hydroxide, potassium hydroxide and a combination thereof; a pH value of the reaction mixture obtained after the quenching is 2-10; the first organic solvent is a halogenated hydrocarbon solvent, an acetate solvent, a substituted benzene solvent or an alkyl ether solvent; the extraction is performed at a temperature of 0-50° C.; and a residence time of the reaction mixture in each extraction separator of the continuous quenching-extraction-separation unit is 0.1-30 minutes.

5. The method of claim 1, wherein in step (3), the acetamidine hydrochloride solution is prepared by dissolving acetamidine hydrochloride with a second alkali-containing organic solution at −20-35° C. and filtration; a molar concentration of acetamidine hydrochloride in the acetamidine hydrochloride solution is 0.5-7 mol/L; an alkali in the second alkali-containing organic solution is selected from the group consisting of sodium hydroxide, potassium hydroxide, sodium methoxide, potassium methoxide, sodium ethoxide, potassium ethoxide, potassium tert-butoxide and sodium tert-butoxide; an organic solvent used in the second alkali-containing organic solution is one or more of C1-C6 fatty alcohols; a molar ratio of the acetamidine hydrochloride to the alkali in the acetamidine hydrochloride solution is 1:0.7-3; and a molar ratio of (dimethylaminomethylene) malononitrile to acetamidine hydrochloride in the (dimethylaminomethylene) malononitrile organic solution is 1:0.6-5.

6. The method of claim 1, wherein in step (3), the continuous oscillating reactor is a continuous flow reactor for three-phase mixing of solid, liquid and gas; and a temperature in the continuous oscillating reactor is −10-65° C.; a residence time of the reaction mixture in the continuous oscillating reactor is 10-120 minutes; the continuous filtration is performed at a temperature of −10-45° C.; and the second organic solvent is one or more of C1-C6 fatty alcohols.

7. The method of claim 1, wherein in step (4), the Raney nickel catalyst is a modified Raney nickel catalyst, a mixture of the modified Raney nickel catalyst and quartz sand, a mixture of the modified Raney nickel catalyst and a molecular sieve, an unmodified Raney nickel catalyst or a mixture of the unmodified Raney nickel catalyst and quartz sand.

8. The method of claim 7, wherein the modified Raney nickel catalyst is a formalin-modified Raney nickel catalyst, and the formalin-modified Raney nickel catalyst is prepared through steps of:
(A) dispersing Raney nickel in a liquid dispersion medium; adding a formalin solution, wherein the formalin solution is 0.5-30% by weight of the Raney nickel; and stirring the reaction mixture at 10-75° C. for 10 minutes to 3 hours in an inert gas; and
(B) filtering the reaction mixture obtained in step (A) to collect a filter residue; and washing the filter residue with deionized water several times to obtain the formalin-modified Raney nickel catalyst followed by storage in water;
wherein a weight ratio of the Raney nickel to the liquid dispersion medium is (0.1-0.65):1; the liquid dispersion medium is water, an organic solvent, or a mixture thereof; the organic solvent is a C1-C4 alkanol selected from the group consisting of methanol, ethanol, ethylene glycol, 1-propanol, 2-propanol, 1,2-propanediol, 1,3-propanediol, 1-butanol and a combination thereof.

9. The method of claim 1, wherein in step (4), an alkali in the (dimethylaminomethylene) malononitrile organic solution is an inorganic base or an organic base; the inorganic base is ammonia water or hydrazine hydrate; and the organic base is selected from the group consisting of methylamine, urea, ethylamine, ethanolamine, ethylenediamine, dimethyl amine, trimethylamine, triethylamine, propylamine, isopropylamine, 1,3-propanediamine, 1,2-propanediamine, tripropylamine, triethanolamine, butylamine, isobutylamine, tert-butylamine, tributylamine, hexylamine, octylamine, aniline, benzylamine, cyclohexylamine and pyridine; and a molar ratio of 2-methyl-4-amino-5-cyanopyrimidine to the alkali is 1: (0.1-10).

10. The method of claim 1, wherein in step (4), a temperature in the third micro-mixer is controlled at 5-150° C.; a temperature in the fixed-bed reactor is controlled at 20-150° C.; flow rates of the reaction mixture entering the third micro-mixer and the hydrogen are adjusted such that a molar ratio of 2-methyl-4-amino-5-cyanopyrimidine to hydrogen is 1: (0.95-1.4); a residence time of the reaction mixture in the fixed-bed reactor is 0.01-60 minutes; and a back pressure valve of the fixed-bed reactor is 0.1-6 MPa.

11. The method of claim 1, wherein the first micro-mixer, the second micro-mixer and the third micro-mixer are independently a static mixer, a T-type micro-mixer, a Y-type micro-mixer, a cross-type mixer, a coaxial flow micro-mixer or a flow-focusing micro-mixer;
the first micro-mixer and the second micro-mixer are both controlled at −10~50° C.;
the microchannel reactor in step (1) is a tubular microchannel reactor or a plate-type microchannel reactor;
the continuous quenching-extraction-separation unit in step (2) is a plate-type microchannel extraction separator, a membrane-type extraction separator or an annulus centrifugal extraction separator;
the continuous oscillating reactor in step (3) is a serial continuous oscillating stirred tank reactor, a continuous oscillatory baffled reactor, or a commercially-available continuous flow reactor capable of achieving full solid-liquid mixing; and
the fixed-bed reactor in step (4) is a jacketed fixed-bed reactor or a non-jacketed fixed-bed reactor.

12. The method of claim 11, wherein an inner diameter of the tubular microchannel reactor is 50 μm-10 mm; wherein the tubular microchannel reactor is a plate-type microchannel reactor, the plate-type microchannel reactor comprises a first heat exchange layer, a reaction layer, and a second heat exchange layer sequentially arranged from top to bottom; the reaction layer is provided with a reaction fluid channel, and a hydraulic diameter of the reaction fluid channel is 50 μm-10 mm;
an inner diameter of the plate-type continuous extraction separator is 100 μm-10 mm, and the plate-type continuous extraction separator comprises a mixing layer and a separation layer; a membrane of the membrane-type extraction separator is a hydrophobic membrane with a pore size of 0.1-4 μm; a diameter of the annulus centrifugal extraction separator is 10 cm-1 m, and one or more plate-type continuous extraction separators or membrane-type extraction separators are connected in series to form the quenching-extraction-separation unit; and
the fixed-bed reactor has an inner diameter of 100 μm-50 cm and a length of 2 cm-50 cm, and one or more fixed-bed reactors are connected in series to form an operating unit.

13. The method of claim 1, wherein in step (1), the micro-reaction system further comprises a first feed pump, a second feed pump, a third feed pump, a fourth feed pump, a fifth feed pump and a back pressure valve; the first feed pump is configured to feed the mixture of cyanoacetamide, N,N-dimethylformamide and the catalyst; the second feed pump is configured to feed phosphorus oxychloride; the third feed pump is configured to feed the aqueous solution of the inorganic base; the fourth feed pump is configured to feed the first organic solvent; the fifth feed pump is configured to feed the second organic solvent; one inlet of the first micro-mixer is connected to first the feed pump, and the other inlet of the first micro-mixer is connected to the second feed pump; an outlet of the first micro-mixer is connected to an inlet of the microchannel reactor, and an outlet of the microchannel reactor is connected to the back pressure valve; an outlet of the back pressure valve is connected to one inlet of the continuous quenching-extraction-separation unit, and the remaining two inlets of the continuous quenching-extraction-separation unit are respectively connected to the third feed pump and the fourth feed pump; a water phase outlet of the continuous quenching-extraction-separation unit is connected to a water phase collection device, and an organic phase outlet is connected to one inlet of the continuous distillation-concentration unit; and the other inlet of the continuous distillation-concentration unit is connected with the fifth feed pump, wherein opening and closing of the other inlet of the continuous distillation-concentration unit is controllable.

14. The method of claim 1, wherein the micro-reaction system further comprises a first feed pump, a second feed pump and a third pump; the first feed pump is configured to feed the acetamidine hydrochloride solution; the second feed pump is connected to an outlet of the continuous distillation-concentration unit; the third feed pump is configured to feed the first alkali-containing organic solution to dissolve the filter cake collected from the continuous filtration unit; one inlet of the second micro-mixer is connected with the first feed pump, the other inlet of the second micro-mixer is connected with the second feed pump; an outlet of the second micro-mixer is connected with an inlet of the continuous oscillating reactor; an outlet of the continuous oscillating reactor is connected to a first port of the continuous filtration unit; a second port of the continuous filtration unit is connected to the third feed pump; a first outlet of the continuous filtration unit is connected to a filtrate collecting device, and a second outlet of the continuous filtration unit is connected to an inlet of the first liquid storage buffer tank; and an outlet of the liquid storage buffer tank is connected to a feed pump of a next microchannel reaction system.

15. The method of claim 1, wherein the micro-reaction system further comprises a feed pump, a gas mass flow controller, a gas-liquid separator, a second liquid storage buffer tank and a back pressure valve; the feed pump is configured to feed the (dimethylaminomethylene) malononitrile organic solution; one inlet of the third micro-mixer is connected to the feed pump, and the other inlet of the third micro-mixer is connected to the gas mass flow controller; the outlet of the third micro-mixer is connected to the fixed-bed reactor; an outlet of the fixed-bed reactor is connected to a first port on a top of the gas-liquid separator, and a second port on the top of the gas-liquid separator is connected to a nitrogen source to provide pressure to the gas-liquid separator; a pressure of the nitrogen is adjustable in a range of 0.01-3.5 MPa; the back pressure valve is connected to a third port on the top of the gas-liquid separator; a back pressure of the back pressure valve is 0.01-3 MPa; the pressure of the nitrogen is 0.02-0.5 MPa greater than the back pressure set by the back pressure valve; and a liquid outlet of the gas-liquid separator is connected to the inlet of the second liquid storage buffer tank.

\* \* \* \* \*